United States Patent [19]

Haber et al.

[11] Patent Number: 4,867,172

[45] Date of Patent: Sep. 19, 1989

[54] COLLAPSIBLE BLOOD COLLECTOR

[75] Inventors: Terry M. Haber, Lake Forest; John A. Lewis, Costa Mesa, both of Calif.

[73] Assignee: Habley Medical Technology Corporation, Laguna Hills, Calif.

[21] Appl. No.: 159,374

[22] Filed: Feb. 23, 1988

[51] Int. Cl.$^4$ .......................... A61B 5/00; A65D 81/00
[52] U.S. Cl. ..................................... 128/763; 604/192; 604/198; 604/263
[58] Field of Search ................................. 128/763–765; 604/110, 192, 197, 198, 263, 762, 766, 767, 770

[56] References Cited

U.S. PATENT DOCUMENTS

| 4,573,976 | 3/1986 | Sampson et al. | 604/198 |
| 4,664,259 | 5/1987 | Landis | 206/365 |
| 4,664,654 | 5/1987 | Strauss | 604/198 |
| 4,731,059 | 3/1988 | Wanderer et al. | 128/764 |
| 4,735,618 | 4/1988 | Hager | 604/198 |
| 4,758,231 | 7/1988 | Haber et al. | 128/763 |

FOREIGN PATENT DOCUMENTS

719635   1/1966  Italy ..................... 604/192

Primary Examiner—Max Hindenburg
Assistant Examiner—K. M. Reichle
Attorney, Agent, or Firm—Morland C. Fischer

[57] ABSTRACT

A low-cost, disposable blood collector which may be collapsed into a low volume disposal package, whereby to maximize both safety and efficiency when discarding the blood collector after use. The blood collector comprises a hollow, collapsible blood collection tube holder for receiving an evacuated blood collection tube, a double-ended hypodermic needle cannula for making a veni puncture and drawing a sample of a patient's blood to a blood collection tube at the interior of the blood collection tube holder, and a collapsible needle cover which surrounds the distal end of the needle cannula. The blood collection tube holder is collapsible from an open, cylindrical configuration, at which to receive a blood collection tube therewithin, to a closed, generally planar configuration, with the blood collection tube removed therefrom. The needle cover is collapsible from an open, expanded configuration, at which the distal end of the needle cannula is exposed for making a veni puncture through the patient's skin, to a closed, generally planar configuration, at which to surround and shield the distal end of the cannula and thereby avoid an accidental needle strike.

19 Claims, 5 Drawing Sheets

COLLAPSIBLE BLOOD COLLECTOR

BACKGROUND OF THE INVENTION

1. FIELD OF THE INVENTION

This invention relates to a disposable and relatively low-cost blood collector that is collapsible into a low volume disposal package which may be safely and efficiently discarded after use while avoiding the spread of a contagious, and possibly life threatening, disease.

2. PRIOR ART

The terror of AIDS has, by necessity, precipitated many advances in the field of infection control, particularly in the field of blood sample safety techniques. The potentially fatal dangers of contaminated blood splashes and accidental needle sticks by contaminated needle cannula are two major causes of nosocomial contamination by AIDS and Hepatitus B viruses.

Techniques have been proposed to isolate contaminated needle cannula and/or blood collection tube holders after use, so as to avoid an accidental needle stick and the spread of a contagious, and possibly life threatening, disease. By way of example, the following U.S. patent applications, which have been or will be assigned to the assignee of the present patent application, disclose a disposable syringe having an outer sleeve which is movable axially relative to an inner needle carrier to surround, shield, and prevent reuse of a needle cannula:

Application Ser. No. 43,042 filed Apr. 27, 1987, now U.S. Pat. No. 4,758,231;

Application Ser. No. 118,745 filed Nov. 9, 1987 now U.S. Pat. No. 4,813,426; and Application No. 118,767 filed Nov. 9, 1987 now U.S. Pat. No. 4,786,827.

Another technique to avoid the spread of a contagious disease by a contaminated needle cannula or blood supply is simply to dispose of the needle cannula and blood collection tube assembly after each use.

Each of the aforementioned techniques requires that health care workers change their thinking toward single use, plastic blood collection tube holders rather than multiple use holders. A blood collection tube holder is a device which is used to support and manipulate the needle cannula and collection tube while a blood sample is being drawn from a "blood precautionary patient". However, with the with instances of patients having a contagious disease, all patients must now be considered as blood precautionary.

Prior to the present re-emphasis on safety, five non-safety blood collection tube holders were commonly packaged in each box of one thousand double-ended blood collection needles. Therefore, it is estimated that each blood collection tube holder was intended to be used for two hundred blood samplings or until the threads in the tube holder failed, whichever occurred first. The practice of utilizing the structure of the blood collection tube holder, itself, to somehow permanently encase a contaminated needle cannula after each blood draw implies an irreversible containment process which irretrievably shields a contaminated needle cannula by contact with, or proximity to, some element of its attached blood collection tube holder on a strictly single-use basis.

The emerging thinking towards single-use blood collection tube holders will do much to minimize the infectious communication of AIDS, Hepatitus B and other dangerous flora. However, a virtually unexpected problem has arisen from these new safety procedures. That is, there has been an exponential increase in the volume of new blood collection tube holders for shipping and dispensing purposes, as well as an even greater increase (because of random packing) in contaminated disposal volume for safe disposal procedures.

For example, prior to the widespread concern for safer blood collection devices and the availability of reliable products to fill this need, pre-existing, conventional blood collection tube holders were used over and over. These reusable blood collection tube holders produced a relatively low contaminated disposal volume of only 0.0066 cubic feet per 1,000 blood draws. However, these same reusable blood collection tube holders caused a highly unsafe condition in terms of re-exposure of the contaminated holders as well as the high risk potential for accidental needle strikes. In the event that the pre-existing conventional blood collection tube holders were not reused and discarded after each use, then a higher contaminated volume of 2.03 cubic feet would result. Nevertheless, the conventional blood collection tube holders would still not protect the health care worker from accidental, contaminated needle stick injuries. Accordingly, it would be desirable to provide a low-cost blood collector that may be disposed after each use, that produces a relatively small contaminated disposal volume, and that is characterized by increased safety and avoidance of an accidental needle stick.

SUMMARY OF THE INVENTION

In general terms, a disposable and relatively low-cost blood collector is disclosed that is collapsible into a low volume disposal package which may be discarded after use with increased safety and maximized efficiency. The blood collector comprises a blood collection tube holder having open proximal and distal ends. An evacuated blood collection tube is received through and supported within the open proximal end of the holder. The blood collection tube holder has a plurality of axially extending and parallel aligned hinges integrally formed around the periphery thereof so as to be collapsible from an open, cylindrical configuration, at which to receive a blood collection tube, to a closed, generally planar configuration, with the blood collection tube removed.

The blood collector also comprises a double-ended hypodermic needle cannula. In one embodiment, where the blood collector is sterilized prior to packaging, the needle cannula is integrally molded to the blood collector. In another embodiment, the needle cannula is a conventional needle having a screw-threaded needle carrying hub to be attached to a complementary screw-threaded needle support of the blood collector. In both embodiments, the needle cannula is retained in coaxial alignment with the blood collection tube holder so that a proximal end of the cannula is positioned to communicate with a blood collection tube at the interior of the holder, and a distal end of the cannula is positioned to make a veni puncture for drawing a sample of a patient's blood.

Surrounding the distal end of the needle cannula is a collapsible needle cover. The needle cover is connected to the distal end of the blood collection tube holder by means of integral, movement translating hinges, so that a one-piece blood collector is formed comprising the collapsible blood collection tube holder and the collapsible needle cover. The needle cover is formed from a plurality of (e.g. four) cover segments. Each cover segment is connected to an adjacent segment by means of an integral hinge, whereby the needle cover is collapsible from an open, expanded configuration, at which the distal end of the needle projects through an orifice in the cover for making a veni puncture through the patient's skin, to a closed, generally planar configuration, at which to surround and shield the distal end of the needle cannula and thereby avoid an accidental needle strike and the spread of a contagious, and possibly life threatening, disease.

A thumb-operated catch is provided to releasably retain the needle cover in the open configuration. A locking tab is also provided to lock the needle cover in the closed configuration at which to surround and shield the needle cannula. The collapsible blood collector, with the blood collection tube holder and needle cover collapsed in the closed configuration, provides a compact disposal package that consumes a relatively small volume so as to be safely and efficiently discarded after a single use while eliminating the high cost and high volume that are commonly associated with blood collection tube holders of the prior art.

DESCRIPTION OF THE PREFERRED EMBODIMENTS

The collapsible blood collector which forms the present invention is now described while referring to the drawings. In accordance with a first embodiment, and referring initially to FIGS. 1-4, a pre-sterilized blood collector 1 is described having an integrally connected needle cannula. More particularly, blood collector 1 includes a hollow, cylindrical blood collection tube holder 2 having open proximal and distal ends. Blood collection tube holder 2 is preferably fabricated from a suitable material, such as radiation grade polypropylene, or the like. Unlike known conventional blood collection tube holders, the presently described blood collection tube holder 2 is collapsible. To this end, the collection tube holder 2 is provided with a series of axially extending integral hinges 4 which permit the holder to assume a collapsed configuration as illustrated in FIGS. 1-4. The integral hinges 4 are formed around the periphery of holder 2 in spaced, parallel alignment with one another. A series of circumferentially extending gripping ridges 5 is formed in blood collection tube holder 2 so as to increase the reliability by which the blood collector 1 may be grasped and operated by a health care worker.

Located at the distal end of blood collection tube holder 2 is a collapsible needle cover 6. Needle cover 6 is defined by distally and proximally oriented pairs of cover segments 8-1 and 8-2. Each cover segment 8-1 and 8-2 is joined to an adjacent segment by means of a respective integral hinge 10, whereby cover 6 may assume a collapsed configuration as illustrated in FIGS. 1-4 Needle cover 6 is connected to the distal end of blood collection tube holder 2 by means of a pair of integral, movement translating hinges 12 which extend, respectively, between opposite sides of the tube holder 2 and the proximal needle cover segments 8-2. Needle cover 6 is provided with a series of gripping ridges 11 along each of the cover segments 8-1 and 8-2, so as to increase the reliability by which cover 6 may be manually manipulated by a health care worker.

Figure 1:
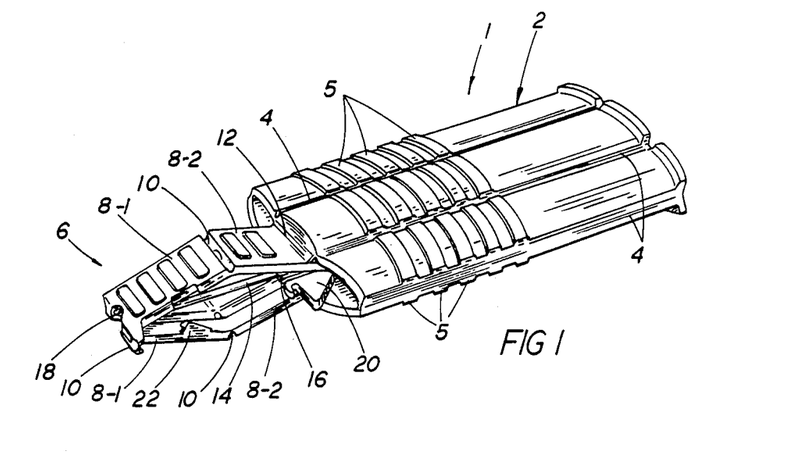
FIG. 1 is an isometric view of the collapsible blood collector according to a first embodiment of the present invention with a blood collection tube holder and a needle cover in a collapsed configuration to form a compact disposal package.
Figure 2:
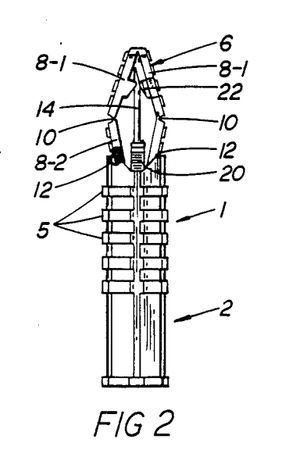
FIG. 2 is a side view of the blood collector of FIG. 1.
Figure 3:
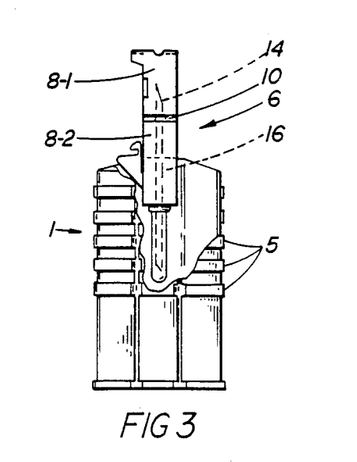
FIG. 3 is a front view partly in section, of the blood collector of FIG. 1.
Figure 4:
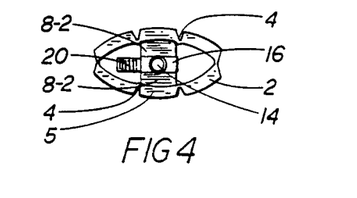
FIG. 4 is a bottom view of the blood collector of FIG. 1.
Figure 5:
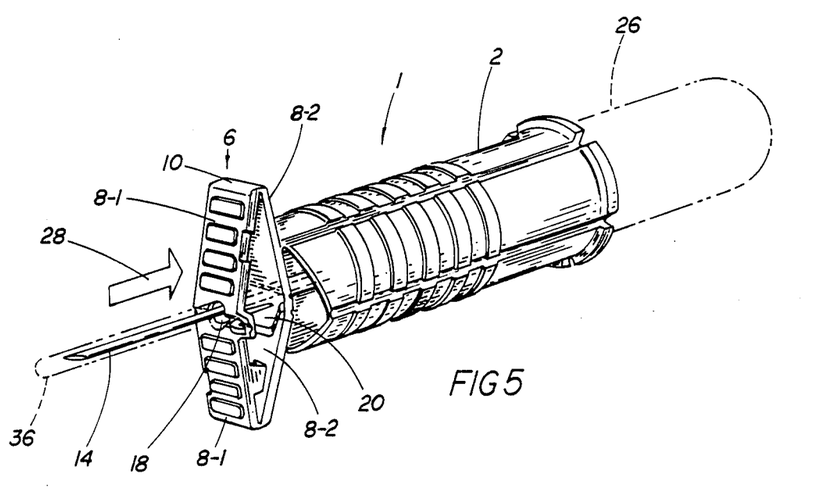
FIG. 5 is an isometric view of the collapsible blood collector of FIG. 1 with the blood collection tube holder and needle cover in an open configuration for drawing a blood sample from a patient into a blood collection tube.
Figure 6:
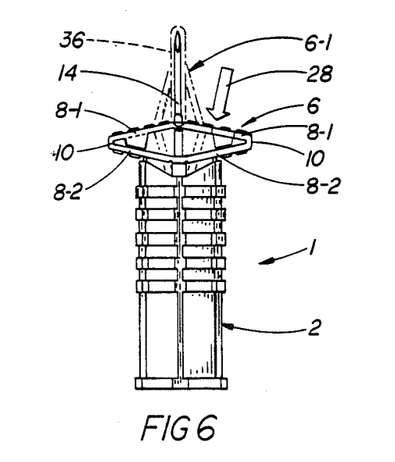
FIG. 6 is a side view of the blood collector of FIG. 5.
Figure 7:
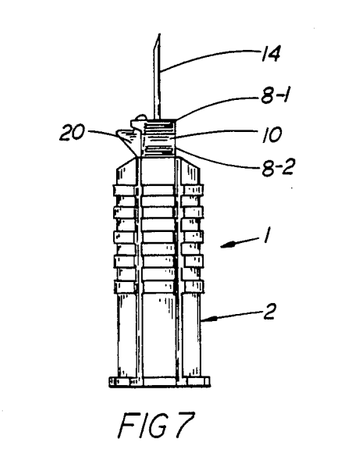
FIG. 7 is a front view of the blood collector of FIG. 5.
Figure 8:
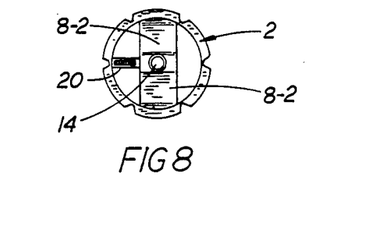
FIG. 8 is a bottom view of the blood collector of FIG. 5.

A double-ended hypodermic needle cannula 14 is retained in coaxial alignment with blood collection tube holder 2 by a needle support plate 16. More particularly, support plate 16 is molded around needle cannula 14. The support plate 16 is also thermally bonded at the intersection of the pair of proximal cover segments 8-2 so that a one-piece, collapsible blood collector assembly is formed comprising blood collection tube holder 2, needle cover 6, and needle cannula 14. As is best shown in FIG. 5, one end of needle 14 projects proximally from needle support plate 16 to communicate with an evacuated blood collection tube 26 at the interior of blood collection tube holder 2. The opposite end of needle 14 projects distally from needle support plate 16 and extends through an orifice 18 that is formed through the hinge 10 at the intersection of the distal cover segments 8-1 of needle cover 6. As will be explained when referring to FIGS. 5-8, the distally projecting end of needle 14 may be suitably positioned to make a veni puncture through the skin of a patient and thereby drawn a sample of the patient's blood.

Coextensively connected to and projecting outwardly from the needle support plate 16 is a thumb-operated catch member 20. As will also be explained when referring to FIGS. 5-8, catch member 20 may be manipulated to engage and releasably retain the needle cover 6 in an open, expanded configuration, whereby needle 14 projects through orifice 18 in cover 6 for making a veni puncture through the patient's skin.

Coextensively connected to and projecting radially from one of the segments (e.g. 8-1) of needle cover 6 is a locking tab 22. As will be explained when referring to FIG. 10, locking tab 22 may be manipulated into engagement with the opposing segment 8-1 of needle cover 6 to retain needle cover 6 in a closed, generally planar configuration, whereby cannula 14 is completely surrounded and shielded by the cover.

FIGS. 5-8 of the drawings show the blood collector 1 in an armed state with the blood collection tube holder 2 in an open, cylindrical configuration to receive blood collection tube 26 and the segmented needle cover 6 in an open, expanded configuration to expose needle 14 through opening 18 for making a veni puncture and thereby drawing a blood sample. More particularly, the blood collection tube holder 2 is opened so that a conventional evacuated blood collection tube (shown in phantom and designated by reference numeral 26) may be located through the proximal end thereof. The receipt of blood collection tube 26 within the hollow interior of tube holder 2 maintains the tube holder in an open configuration. An axial and proximally directed force (represented by the arrows 28 of FIGS. 5 and 6) is applied to the distal segments 8-1 of needle cover 6 to cause the cover segments 8-1 and 8-2 to rotate around their respective integral hinges 10 and thereby expand the cover 6 from the closed, generally planar configuration (shown in phantom in FIG. 6 and represented by the reference numeral 6-1) to the open configuration. Accordingly, the proximally projecting end of needle cannula 14 communicates the blood collection tube 26 at the interior of the open blood collection tube holder 2. The distally projecting end of needle cannula 14 extends through the orifice 18 between the distal cover segments 8-1 for making a veni puncture through the patient's skin. A standard, removable needle sheath 36 surrounds the distally projecting end of needle cannula 14 to prevent an accidental needle strike prior to making the veni puncture. As is best shown in FIG. 5, the thumb-operated catch 20 is manipulated (i.e. rotated) into engagement with the distal cover segments 8-1 to reliably and releasably retain the cover 6 in the open, expanded configuration while one or more samples of the patient's blood are successively drawn into respective blood collection tubes 26 via cannula 14. After the last blood sample has been taken, the blood collection tube 26 is removed from the blood collection tube holder 2 and the sample is centrifuged for subsequent study.

Figure 9:
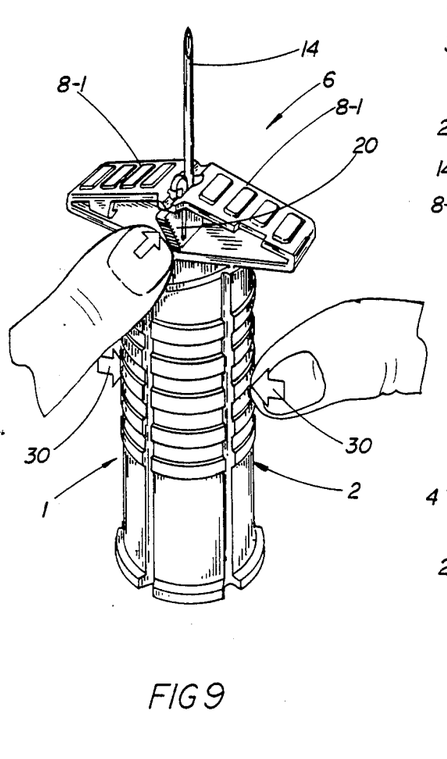
FIG. 9 shows the blood collector of FIG. 1 in an armed state for making a veni puncture.
Figure 10:
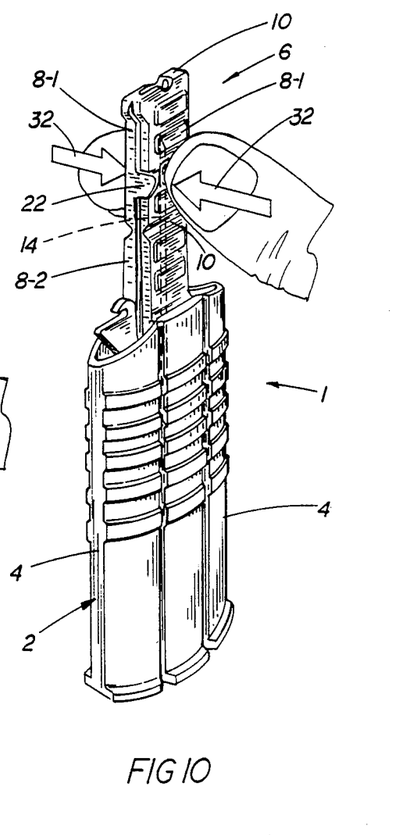
FIG. 10 shows the blood collector in a shielded state for safe and efficient disposal.

Referring to FIGS. 9 and 10 of the drawings, the blood collector 1 is then released from the armed state (of FIG. 9) to a shielded state (of FIG. 10) so as to form a compact disposal package with cannula 14 safely surrounded and shielded by needle cover 6. More particularly, the health care worker grasps the blood collection tube holder 2 in one hand and, with the thumb of the other hand, releases the thumb-operated catch member 20. That is, the catch member 20 is rotated out of engagement with the distal segments 8-1 of cover 6 to release the cover from the open, expanded configuration. The health care worker uses his thumb and index finger to exert equal and opposite, laterally directed forces upon the blood collection tube holder 2 (in the direction indicated by reference arrows 30 of FIG. 9) by which to compress the tube holder 2.

Accordingly, the blood collection tube holder 2 is collapsed at a pair of oppositely disposed, integral hinges 4 from the open, cylindrical configuration of FIG. 9 to the closed, generally planar configuration of FIG. 10. The health care worker then slides his thumb and index finger upwardly from tube holder 2 to the needle cover 6. Equal and opposite laterally directed forces are exerted upon a pair of the cover segments (e.g. 8-1) in the direction of the reference arrows 32, whereby to compress the cover 6. Accordingly, the segments 8-1 and 8-2 of needle cover 6 are rotated around their integral hinges 10 for collapsing cover 6 from the open, expanded configuration of FIG. 9 to the closed, generally planar configuration of FIG. 10.

The locking tab 22 is then extended between and snapped across distal cover segments 8-1 to thereby lock the collapsible blood collector 1 in the shielded state (of FIG. 10) while preventing an inadvertent return to the armed state (of FIG. 9). Thus, in the shielded state of FIG. 10, the segments 8-1 and 8-2 of needle cover 2 are folded around the distally extending end of needle cannula 14 so as to completely surround and shield the cannula and thereby avoid an accidental needle strike and the spread of a contagious, and possibly life threatening, disease. Morever, the blood collection tube holder 2 is collapsed to form a relatively low volume disposal package which may be safely and efficiently discarded after use.

Figures 11, 12, 13, 14:
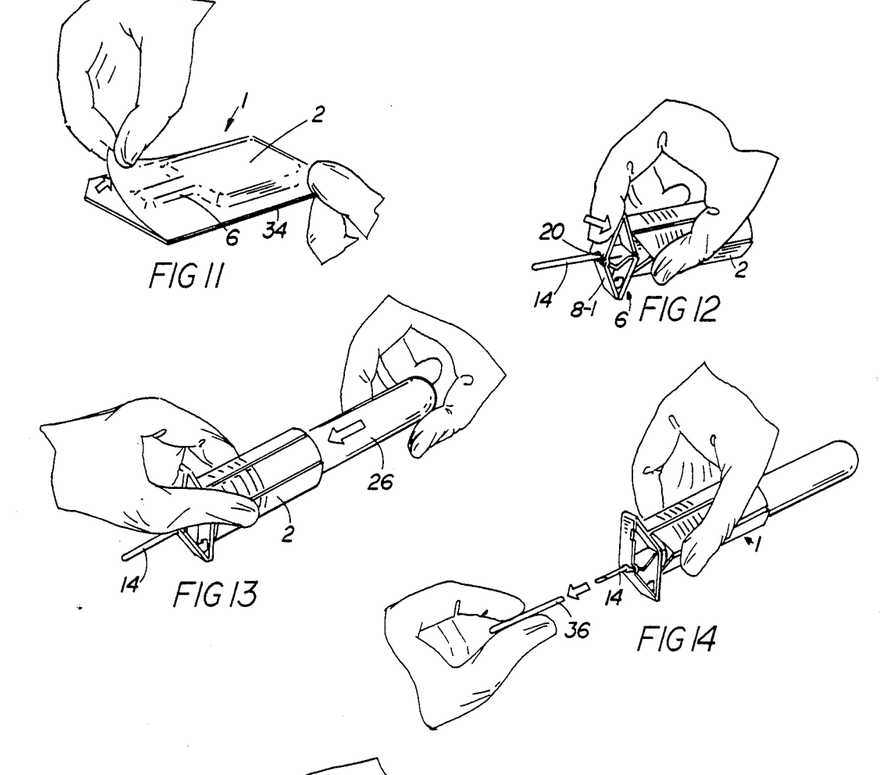
FIG. 11-17 illustrate the steps for operating the blood collector of FIG. 1.

The operation of the collapsible blood collector 1 (with the integral needle cannula of the first embodiment) is detailed while referring to FIGS. 11-17 of the drawings. FIG. 11 shows the collapsible, pre-sterilized blood collector 1, as packaged for transport to and storage at a medical facility. Blood collector 1 is packaged in the shielded state (similar to that shown in FIG. 10) with both the blood collection tube holder 2 and the needle cover 6 being retained in a closed, generally planar configuration. Blood collector 1 is packaged with the protective sheath (designated 36 in FIG. 14) surrounding the distal end of cannula 14 to preserve the sterility thereof and avoid an accidental needle strike.

The blood collector 1 is removed from its package 34 and locked in the armed state. More particularly, and referring to FIG. 12, the health care worker applies an axial and proximally directed force to the distal segments 8-1 of needle cover 6 to expand cover 6 and open blood collection tube holder 2. The thumb-operated catch member 20 is rotated into engagement with the cover 6 (as previously explained when referring to FIG. 5) to retain cover 6 and tube holder 2 in the open configuration with the needle cannula 14 exposed and projecting distally through the opening 18 in cover 6.

In FIG. 13, an evacuated blood collection tube 26 is moved through the proximal end of blood collection tube holder 2 and into communication with the proximally extending end of needle cannula 14 at the interior of tube holder 2. In FIG. 14, the protective sheath 36 is removed from the distally extending end of needle cannula 14 and discarded. As is illustrated in FIG. 15, the cannula 14 of blood collector 1 is then located to make a veni puncture through the skin of the patient to automatically draw one or more blood samples of the patient's blood into a corresponding number of evacuated blood collection tubes 26.

Figures 15, 16, 17:
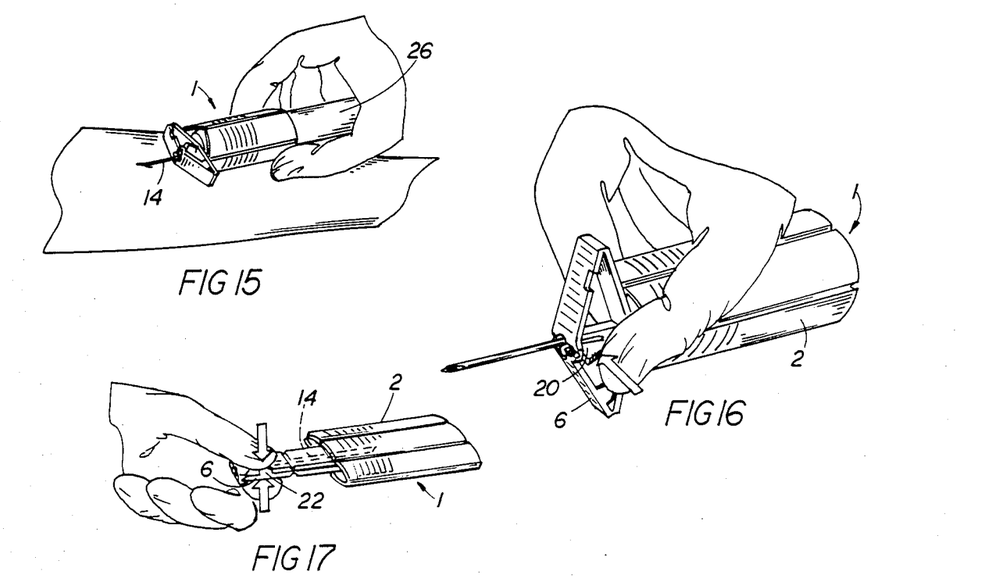

In FIGS. 16 and 17, the blood collection tube 26 is removed, so that the blood collector 1 can be returned to the shielded state with both the blood collection tube holder 2 and needle cover 6 collapsed and locked in a closed, generally planar configuration (like that illustrated in FIG. 10). More particularly, the health care worker uses his thumb (in FIG. 16) to rotate catch member 20 out of engagement with needle cover 6 to thereby release the cover from its open, expanded configuration. In FIG. 17, the health care worker uses his thumb and index finger to apply equal and opposite, laterally directed forces to needle cover 6, whereby to compress and thereby collapse both the needle cover 6 and the blood collection tube holder 2. The locking tab 22 is then closed across the needle cover 6 (as previously disclosed when referring to FIG. 10) to lock the blood collector 1 in the shielded state with the hinged segments of the collapsible needle cover 6 completely surrounding and shielding the needle cannula 14. Accordingly, the blood collector 1 may be safely discarded in a compact package which comsumes a relatively small volume and avoids the risk of an accidental needle strike and the spread of a contagious, and possibly life threatening, disease.

Figure 18:
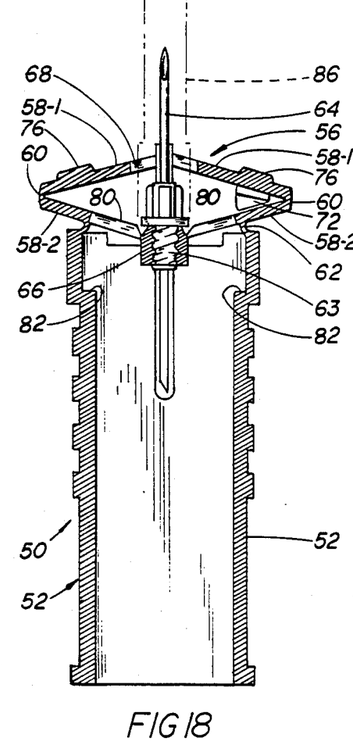
FIG. 18 is a cross-section of a collapsible blood collector according to a second embodiment of the present invention with a blood collection tube holder and a needle cover in an open configuration.
Figure 19:
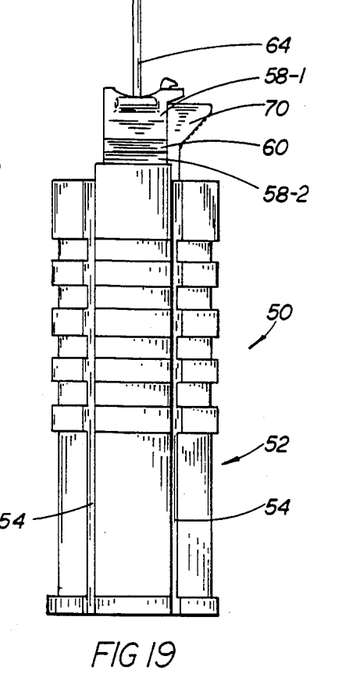
FIG. 19 is a side view of the blood collector of FIG. 18.
Figure 20:
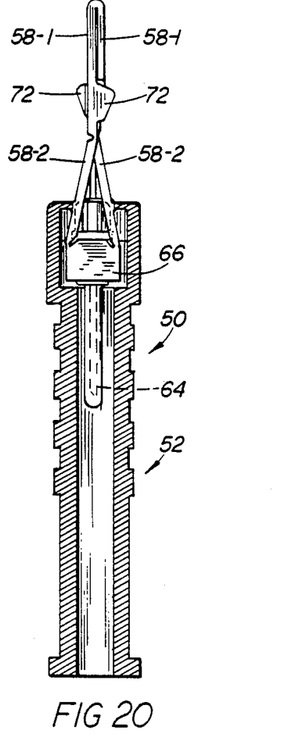
FIG. 20 is a cross-section through the front of the blood collector of FIG. 18 with the blood collection tube holder and needle cover in a collapsed configuration to form a compact disposal package.
Figure 21:
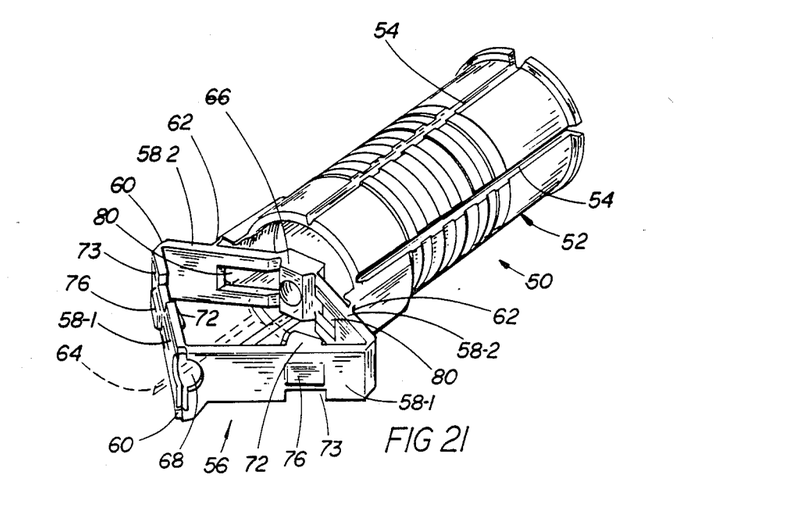
FIG. 21 is an isometric view of the blood collector of FIG. 18 in the open configuration.

In accordance with a second embodiment of the present invention and referring concurrently to FIGS. 18–21 of the drawings, a collapsible blood collector 50 is described which is adapted to receive a conventional needle (rather than the integrally molded needle 14 of FIGS. 1–17). The blood collector 50 is substantially identical to the previously described blood collector 1. That is, blood collector 50 includes a hollow, cylindrical blood collection tube holder 52 having open proximal and distal ends and a series of axially extending and parallel aligned integral hinges 54 which extend around the periphery of tube holder 52 and permit the holder to collapse from an open, cylindrical configuration (as shown in FIGS. 18, 19 and 21) to a closed, generally planar configuration (as shown in FIG. 20). Located at the distal end of blood collection tube holder 52 is a collapsible needle cover 56. Needle cover 56 is defined by distally and proximally oriented pairs of cover segments 58-1 and 58-2. Each cover segment 58-1 and 58-2 is connected to an adjacent segment by means of a respective, integral hinge 60. Needle cover 60 is connected to the distal end of blood collection tube holder 52 by means of a pair of integral movement translating hinges 62 which extend respectively between opposite sides of the tube holder and the proximal needle cover segments 58-2. A finger pad 76 projects upwardly from each of the distal needle cover segments 58-1 to facilitate collapsing the needle cover 56 by a health care worker from the open, expanded configuration to the closed, generally planar configuration.

A screw-threaded needle carrying hub 63 is received by a threaded base segment 66 to support a double-ended needle cannula 64 in coaxial alignment with blood collection tube holder 52. That is to say, screw threaded hub 63 is mated to screw-threaded base segment 66 so that blood collector 50 may be interfaced with a standard double-ended needle cannula 64. One end of needle cannula 64 extends proximally from hub 63 to communicate with an evacuated blood collection tube (not shown) at the interior of blood collection tube holder 52. The opposite end of needle cannula 64 projects distally from hub 63 and extends through an opening 68 that is formed at the intersection of the distal cover segments 58-1 of needle cover 56 so as to be exposed for making a veni puncture through the patient's skin and drawing a sample of the patient's blood. The distally extending end of cannula 64 is shown in FIG. 18 surrounded by a disposable needle sheath 56 prior to making a veni puncture and drawing a blood sample.

Blood collector 50 includes a thumb-operated catch 70 and a locking tab 72 which perform similar functions to the catch member 20 and locking tab 22 that were previously described when referring to the FIGS. 1–17. More particularly, the thumb-operated catch member 70 extends outwardly from needle base support 66 to be manually manipulated (i.e. rotated) into engagement with to thereby releasably retain the needle cover 56 in the open, expanded configuration, so that one or more blood samples may be successively drawn into respective blood collection tubes via cannula 64. A locking tab 72 projects from each of the distal needle cover segments 58-1, so as to be received through a respective notch 73 formed in the opposite distal cover segment. Thus, and as is best represented in FIG. 20, when the cover segments 58-1 and 58-2 of needle cover 56 are rotated at their respective hinges 60 so that cover 56 is collapsed from the expanded to the closed configuration, each locking tab 72 engages its opposite distal cover segment 58-1 in order to lock the needle cover 56 in the closed configuration with cover segments 58-1 and 58-2 completely surrounding and shielding the needle cannula 64 to avoid an accidental needle strike and the spread of a contagious, and possibly life threatening, disease.

To minimize the volume of the disposal package when the blood collector 50 is collapsed and locked (by means of locking tabs 72) in the shielded state of FIG. 20, a cutout 80 is formed through each of the proximal needle cover segments 58-2. Accordingly, when the needle cover 56 is collapsed to the closed, generally planar configuration, opposite ends of the threaded base segment 66 (which receives needle carrying hub 63 therein) can be received through cutouts 80. Therefore, not only is a low volume disposal package established, but a more reliable shield can be formed around cannula 64 by needle cover segments 58-1 and 58-2.

What is even more, the blood collection tube holder 52 of blood collector 50 is formed with a pair of oppositely disposed hollow cupping areas 82 (best illustrated in FIG. 18). Each cupping 82 creates a slightly expanded volume in the opposing front and back surfaces of blood collection tube holder 52. Accordingly, when the needle cover 56 is collapsed to the closed, generally planar configuration of FIG. 20, the cupping areas 82 will enclose the opposite ends of the threaded base segment 66 which are received through cutouts 80. In this manner, a more compact disposal package is possible, whereby to minimize the disposal volume and maximize the safety provided when needle cover 56 is locked in the closed configuration around needle cannula 64. Hence, and by virtue of the present invention, a single use, disposable blood collector is available which is characterized by a reduced cost per blood draw when compared with conventional disposable blood collectors.

The operation of the blood collector 50 illustrated in FIGS. 18–21 is substantially the same as the operation of the blood collector 1 described when referring to FIGS. 11–17. Therefore, for purposes of brevity, the operation of blood collector 50 will not be described herein.

It will be apparent that while preferred embodiments of the invention have been shown and described, various modifications and changes may be made without departing from the true spirit and scope of the invention. Having thus set forth the preferred embodiments, what is claimed is:

1. A collapsible blood collector comprising:

blood collection tube receiving means having proximal and distal ends for receiving a blood collection tube through said proximal end;

means to retain a hypodermic needle cannula having proximal and distal ends, such that the proximal end of the cannula is positioned to communicate with a blood collection tube at the interior of said blood collection tube receiving means, and the distal end of the cannula is positioned to make a veni puncture through a patient's skin; and needle cover means movable from a first position, at which to surround and shield the distal end of the needle cannula and thereby avoid an accidental needle strike, to a second position, at which to expose the cannula for making a veni puncture;

said blood collection tube receiving means being collapsible from an open, cylindrical configuration, at which a blood collection tube may be received therewithin, to a closed, generally planar configuration at which the blood collection tube is removed therefrom and may not be received therewithin.

2. The collapsible blood collector recited in claim 1, wherein said collapsible blood collection tube receiving means has a plurality of axially extending, parallel aligned hinges and a plurality of axially extending, parallel, movable sections that are interconnected with one another by said hinges, said tube receiving means being collapsible at said hinges.

3. The collapsible blood collector recited in claim 2, wherein said axially extending hinges are integrally connected to the movable sections of said blood collection tube receiving means.

4. The collapsible blood collector recited in claim 1, wherein said needle cover means is collapsible from an open, expanded configuration, at which to expose the distal end of the needle cannula for making a veni puncture, to a closed, generally planar configuration, at which the distal end is surrounded and shielded.

5. The collapsible blood collector recited in claim 4, further comprising catch means to releasably retain said needle cover means in the open configuration with the distal end of the needle cannula exposed for making a veni puncture.

6. The collapsible blood collector recited in claim 4, further comprising locking tab means to lock said needle cover means in the closed configuration with the distal end of the needle cannula surrounded and shielded.

7. The collapsible blood collector recited in claim 4, further including opening means through which the distal end of the needle cannula extends so as to be exposed for making a veni puncture when said cover means is in the open configuration.

8. The collapsible blood collector recited in claim 7, wherein said needle cover means comprises pairs of generally planar, proximal and distal cover segments and a plurality of hinges, the distal ends of said distal cover segments being pivotally connected to one another, each proximal end of said distal cover segments being pivotally connected to the distal end of the adjacent proximal cover segment and each proximal end of said proximal cover segments being pivotally connected to the distal end of the blood collector tube receiving means by means of a respective hinge for forming a protective covering around the distal end of the needle cannula when said needle cover means is in the closed configuration, said needle cover means being collapsible into the closed configuration at said hinges.

9. The collapsible blood collector recited in claim 8, wherein said hinges are integrally formed between adjacent segments of said needle cover means.

10. The collapsible blood collector recited in claim 4, wherein said needle cover means is hingedly connected to the distal end of said blood collection tube receiving means.

11. A collapsible blood collector comprising:

blood collection tube receiving means having proximal and distal ends for receiving a blood collection tube through said proximal end, said blood collection tube receiving means being collapsible from an open, cylindrical configuration, at which a blood collection tube may be received therewithin, to a closed, generally planar configuration at which the blood collection tube is removed therefrom and may not be received therewithin;

means to retain a hypodermic needle cannula having proximal and distal ends, such that the proximal end of the cannula is positioned to communicate with a blood collection tube at the interior of said blood collection tube receiving means, and the distal end of the cannula is positioned to make a veni puncture through a patient's skin; and needle cover means being in receipt of and movable relative to the needle cannula, said needle cover means being collapsible from an open, expanded configuration, at which the distal end of the cannula is exposed for making a veni puncture through the patient's skin, to a closed, generally planar configuration, at which the distal end of the cannula is surrounded and shielded to thereby avoid an accidental needle strike.

12. The collapsible blood collector recited in claim 11, wherein said needle cover means is connected to said blood collection tube receiving means.

13. The collapsible blood collector recited in claim 12, further comprising force translating hinge means by which said needle cover means is connected to said blood collection tube receiving means.

14. The collapsible blood collector recited in claim 11, wherein said collapsible blood collection tube receiving means has a plurality of axially extending, parallel aligned hinges and a plurality of axially extending, parallel, movable sections that are interconnected with one another by said hinges, said tube receiving means being collapsible at said hinges.

15. The collapsible blood collector recited in claim 14, wherein said axially extending hinges are integrally formed with the movable sections of said blood collection tube receiving means.

16. The collapsible blood collector recited in claim 11, further comprising catch means to releasably retain said needle cover means in the open configuration with the distal end of the needle cannula exposed for making a veni puncture.

17. The collapsible blood collector recited in claim 11, further comprising locking tab means to lock said needle cover means in the closed configuration with the distal end of the needle cannula surrounded and shielded.

18. The collapsible blood collector recited in claim 11, further including opening means through which the distal end of the needle cannula extends so as to be exposed for making a veni puncture when said cover means is in the open configuration.

19. The collapsible blood collector recited in claim 18, wherein said needle cover means comprises pairs of generally planar, proximal and distal cover segments and a plurality of hinges, the distal ends of said distal cover segments being pivotally connected to one another, each proximal end of said distal cover segments being pivotally connected to the distal end of the adjacent proximal cover segment and each proximal end of said proximal cover segments being pivotally connected to the distal end of the blood collector tube receiving means by means of a respective hinge for forming a protective covering around the distal end of the needle cannula when said needle cover means is in the closed configuration, said needle cover means being collapsible into the closed configuration at said hinges.

* * * * *